Figure 1:
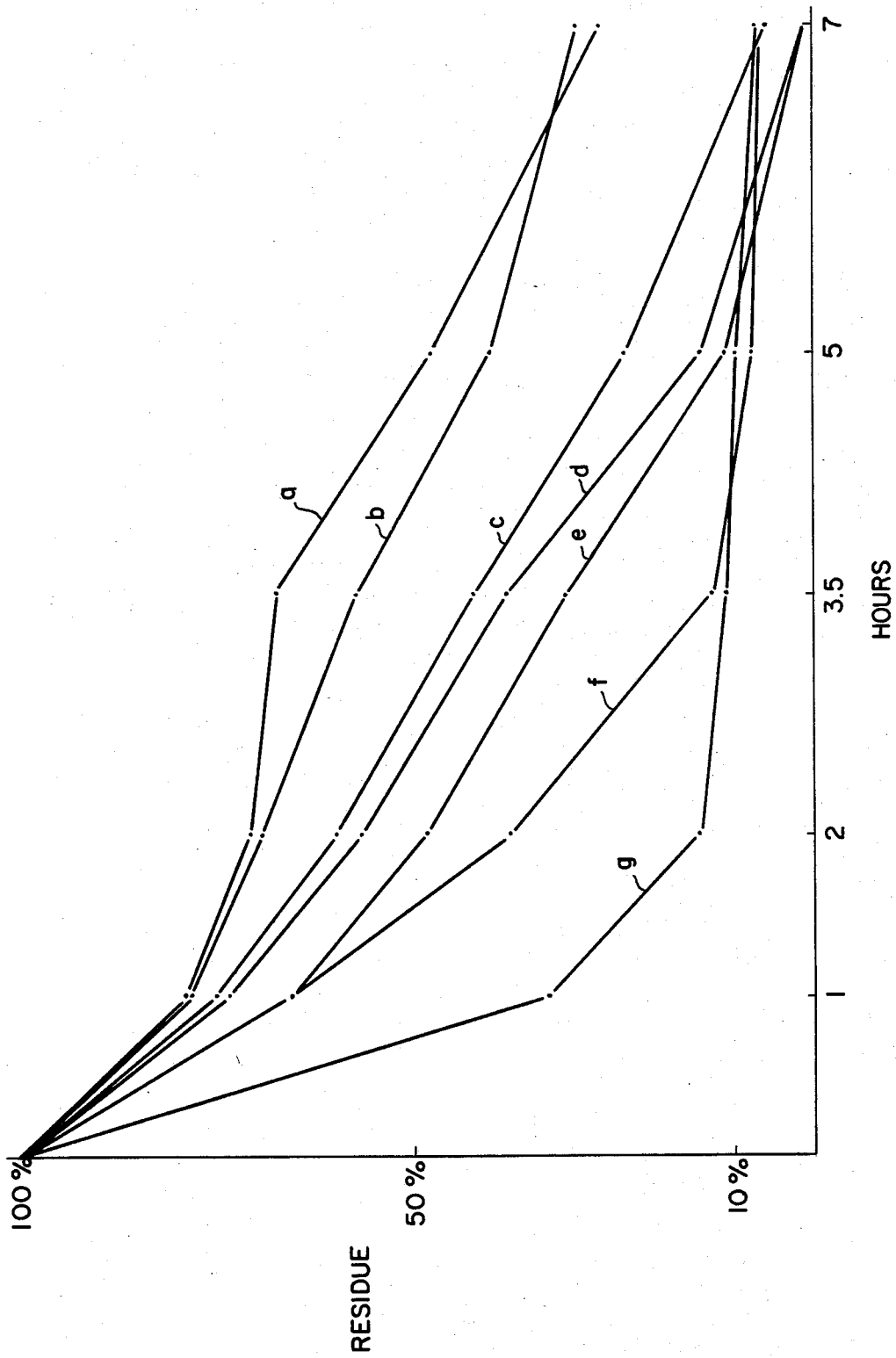

United States Patent [19]
Knecht et al.

[11] Patent Number: 4,608,248
[45] Date of Patent: Aug. 26, 1986

[54] PROCESS FOR TIME-CONTROLLED RELEASE OF ACTIVE INGREDIENTS

[75] Inventors: Adolf Knecht, Freiburg; Helmut Augart, Waldkirch, both of Fed. Rep. of Germany

[73] Assignee: Warner-Lambert Company, Morris Plains, N.J.

[21] Appl. No.: 833,430

[22] Filed: Feb. 24, 1986

Related U.S. Application Data

[63] Continuation of Ser. No. 795,756, Nov. 8, 1985, abandoned, which is a continuation of Ser. No. 391,020, Jun. 22, 1982, abandoned.

[51] Int. Cl.$^4$ .......................... A61K 9/22; A61K 9/26
[52] U.S. Cl. .......................................... 424/19; 424/22
[58] Field of Search ..................................... 424/19–22

[56] References Cited

U.S. PATENT DOCUMENTS

| | | | |
|---|---|---|---|
| 2,805,977 | 9/1957 | Robinson et al. | 424/38 |
| 2,875,130 | 2/1959 | Grass et al. | 424/21 |
| 3,062,720 | 11/1962 | Costello | 424/22 |
| 3,065,143 | 11/1962 | Christenson et al. | 424/19 |
| 3,108,046 | 10/1963 | Harbit | 424/38 |
| 3,133,863 | 5/1964 | Tansey | 424/19 |
| 3,147,187 | 9/1964 | Playfair | 424/17 |
| 3,279,998 | 10/1966 | Raff et al. | 424/22 |
| 3,402,240 | 9/1968 | Cain et al. | 424/22 |
| 3,577,514 | 5/1971 | Robinson | 424/19 |
| 3,689,674 | 9/1972 | Kabbe et al. | 424/326 |
| 4,167,558 | 9/1979 | Sheth et al. | 424/19 |

FOREIGN PATENT DOCUMENTS 0068446 12/1985 European Pat. Off. .

OTHER PUBLICATIONS

Chemical Abstracts, Pharmacodynamics, vol. 79, 1973, p. 25, Abstract 61534E.

*Primary Examiner*—Shep K. Rose
*Attorney, Agent, or Firm*—Ronald A. Daignault

[57] ABSTRACT

The present invention provides a process for the timed control of the liberation of active material from a retarded active material-containing composition by the addition of a hydrophilic polymer, wherein the rate of liberation is adjusted by means of the viscosity of the added hydrophilic polymer, the rate of liberation increasing with increasing viscosity.

2 Claims, 6 Drawing Figures

PROCESS FOR TIME-CONTROLLED RELEASE OF ACTIVE INGREDIENTS

CROSS REFERENCE TO RELATED APPLICATIONS

This is a continuation of U.S. Ser. No. 795,756 of Nov. 8, 1985, which, in turn is a continuation of U.S. Ser. No. 391,020 filed June 22, 1982, and both now abandoned.

The present invention is concerned with a process for the timed control of the liberation of active materials from active material-containing compositions and especially from pharmaceutical compositions.

In pharmaceutical technology, it is known to incorporate active materials into pharmaceutical compositions in such a manner that the active materials are liberated from these compositions at a predetermined rate. In this way, it is possible, for example, to achieve a prolongation of the period of action and thus to avoid too quick and/or too concentrated a release of the active material and too high peaks of the blood or tissue levels, which can lead to undesirable side effects.

If the good solubility or, in the case of peroral pharmaceutical products, also the good resorbability of the active material is the reason for too rapid a release, then the resorption of such an active material can be retarded by restricting the original solubility properties. In the simplest case, they can be achieved, for example, in the case of readily soluble substances by admixing poorly soluble adjuvant materials or by coating the substances with adjuvant materials which lower the solubility. Generally speaking, the rule applies that readily water-soluble substances must be worked up with poorly soluble adjuvant materials and poorly water-soluble substances with readily soluble or readily swellable adjuvant substances if a good retarding effect is to be achieved. Such compositions are often additionally coated with diffusion coatings.

It is known that hydrophilic polymers can be used to produce the desired retarding effect.

From J. Pharm. Sci., 55, 974/1966, it is known, for example, that the desired retarding effect depends exclusively upon the formation of a viscous gel barrier which prevents the penetration of digestive juices into the interior of tablets.

Otherwise, hydrophilic polymers have hitherto only been used in pharmaceutical technology as binding agents in aqueous solution for achieving mechanically stable compressed bodies and those with a high swellability have been employed as so-called disintegrating agents for achieving a rapid breakdown of tablets in solid form.

For the expert, it was hitherto very difficult, when using swelling materials, for example guar gum, carob bean meal, semi-synthetic or synthetic polymers, such as silicic acids, cellulose acetate phthalate, hydroxypropylcellulose or carboxypolymethylene (Carbopol), to predict their influence on the liberation of an active substance from a pharmaceutical composition and hitherto extensive empirical experiments were first necessary in order to develop a retard form with a previously determined liberation characteristic of the active material.

It is an object of the present invention to adjust the liberation characteristic of retard form with the simplest of means in any desired manner, using a previously unknown principle, and thus to minimise the empirical experiments in the case of developments.

We have now, surpisingly, found that when using hydrophilic polymers, especially carboxymethylcellulose and methylcellulose, the differences of solubility or a swellability, due, perphaps, to the degree of substitution, have only a very small influence on the liberation of active materials from retard pharmaceutical compositions.

The expert would, on the basis of his knowledge of the prior art, actually have expected that in the case of the incorporation of, for example, carboxymethylcellulose into retard compositions, the degree of substitution would be of considerable importance for the aberosion of compressed bodies and thus the liberation of active material involved therewith since the solubility or swellability of this adjuvant material depends directly upon the degree of substitution so that, upon contact with water or digestive juices, due to varyingly strong swelling and loosening up of the pharmaceutical compositions, a greatly differing rate of liberation ought to result. Completely unexpectedly, we have found that the liberation of the active material is essentially determined only by the degree of viscosity of the added hydrophilic polymers, the adjustment of a less retarded liberation of active material taking place, fully surprisingly, with highly viscous polymers, whereas with low viscous polymers the liberation of the active material is more strongly retarded.

Consequently, according to the present invention, there is provided a process for the timed control of the liberation of active material from a retarded active material-containing composition and especially from a pharmaceutical composition by the addition of a hydrophilic polymer, wherein the rate of liberation is adjusted by means of the viscosity of the added hydrophilic polymer, the rate of liberation increasing with increasing viscosity.

Especially preferred hydrophilic polymers include carboxymethylcelluloses (synonym: sodium carboxymethylcellulose, CMC, Na-celluloseglycolate) and methyl cellulose, which are widely available commercially. They differ, on the one hand by the degree of substitution and, on the other hand, within a certain range of substitution, by the viscosity which, in turn, is dependent upon the degree of polymerisation or upon the molecular weight. The viscosity of the conventional commercial products is determined in aqueous solution and is type-specified by the manufacturer. The statements in the present description refer to the data supplied by the manufacturer and depend upon the viscosity determination, published in the Company's brochure of technical data for cellulose gum and its chemical and physical properties (cellulose gum No. 800-6A/G, Hercules, Wilmington, Del., U.S.A.).

Not only by the use of hydrophilic polymers of quite definite viscosity but also by the use of mixtures of polymers with different degrees of viscosity, the rate of liberation of active materials from solid retard compositions can now be varied and fixed in a previously unknown manner. In the case of the use of a thorough mixing of, for example, carboxymethylcelluloses of differing viscosity, retard products are obtained, the course of liberation of which lies between the courses of liberation which the individual components would have given.

Carboxymethylcelluloses are, therefore, especially preferred for the process according to the present invention because these are commercially available in a large number of degrees of viscosity of from about 0.02 Pa.s to about 40 Pa.s. and do not give rise to any problems with regard to their stability and compatibility with active materials and other adjuvant materials.

The process according to the present invention is advantageous for the development of retard pharmaceutical compositions since the carrying out of a large number of experiments can be avoided. Hitherto, in large series of experiments, it was necessary to find compositions which gave the necessary liberation of the active materials. The formulations were thereby either randomly selected and varied within the series of experiments or, according to a factor search plan, certain influential factors were sought, each of which had to be varied at different levels. The planned experiments must thereby be carried out, the products obtained investigated and, on the basis of the results, the selection made for the next series of experiments.

When using the process according to the present invention, this work is, as a rule, either not necessary or is substantially reduced in extent; thus, after one preliminary experiment, the probably suitable viscosity stage of, for example, carboxymethylcellulose, can be sought. It the desired degree of active material liberation is thereby not obtained, then, by the use of mixtures of carboxymethylcelluloses with different degrees of viscosity, an appropriate degree of liberation can be adjusted.

If this adjustment has taken place, then products are obtained, each of which are the same in their qualitative and quantitative composition and which only differ by the degree of viscosity of the carboxymethylcelluloses employed.

Since the products are of uniform composition, the working up properties are also the same. Thus, there is no danger that, in the case of variation of the degree of liberation, as previously, the physical properties, for example, the tabletability, would also change. The active material stability of such products is also the same for all degrees of viscosity and, consequently, no longer has to be separately determined for each variation in prolonged stability tests.

The amount of polymer to be added is, as a rule, from 0.1 to 10% by weight of the total mass of the composition. When using carboxymethylcelluloses, amounts in the range of from 0.5 to 3% by weight are preferred.

The process according to the present invention can, in principle, also be applied to other active material-containing compositions, for example, animal bait, fertilisers and herbicides.

The following Examples are given for the purpose of illustrating the present invention:

EXAMPLE 1

100 g. of hydrogenated castor oil, 150 g. of stearic acid and 750 g. lactose were homogeneously mixed with 10 g. amounts of carboxymethylcellulose of various stages of viscosity and then melt granulated in known manner. The following viscosity stages were thereby employed:

(a) 0.05 Pa.s.
(b) 0.3 Pa.s.
(c) 0.6 Pa.s.
(d) 3 Pa.s.
(e) 6 Pa.s.
(f) 20 Pa.s.
(g) 40 Pa.s.

All batches were then pressed with a medium, uniform pressure to give domed tablets of 11 mm. diameter and 490 mg. weight. The breakdown of the tablets was investigated by the procedure described in the National Formulary XIV, p.985, in simulated gastric and duodenal juice, based upon their loss of weight, the residues of the tablets being determined at time intervals indicated on the abscissa of FIG. 1 of the accompanying drawings, dried at 45° C. for 10 hours and weighed.

It can be seen from FIG. 1 that the weight loss of the tablets is directly dependent upon the viscosity of the carboxymethylcellulose used.

EXAMPLE 2

This Example demonstrates the adjustment of a particular active material liberation on the basic of a predetermined specification.

Figure 2A:
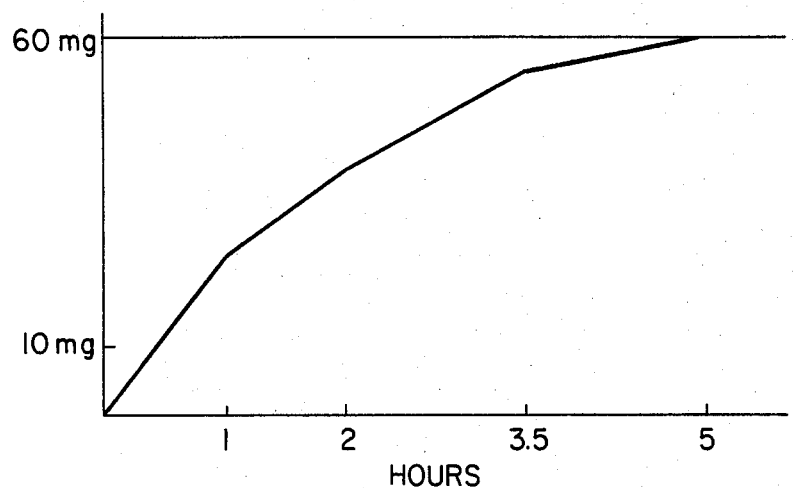
Figure 2B:
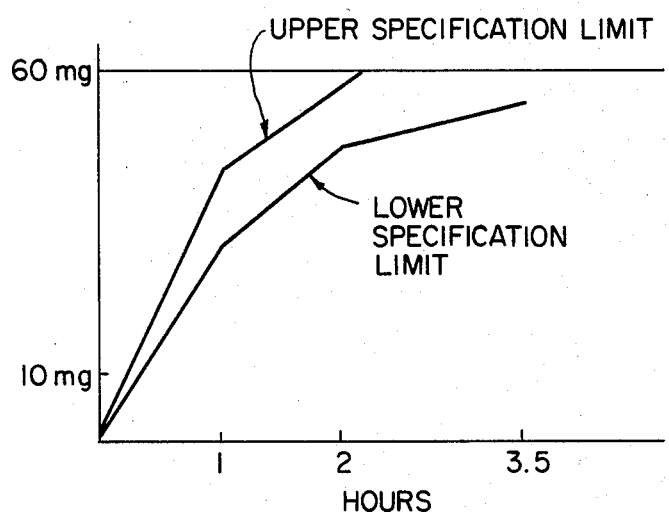

In the manner described in Example 1, tablets were produced with a total weight of 300 mg. and with an active material content of 60 mg. (diltiazem hydrochloride). The determination of the active material was made from the liquid medium at the time intervals indicated on the abscissa of FIG. 2a of the accompanying drawings. Initially, use was made of a carboxymethylcellulose with a viscosity of 0.3 Pa.s., the results obtained being given in FIG. 2a. The desired limits of liberation are shown in FIG. 2b.

Figure 2C:
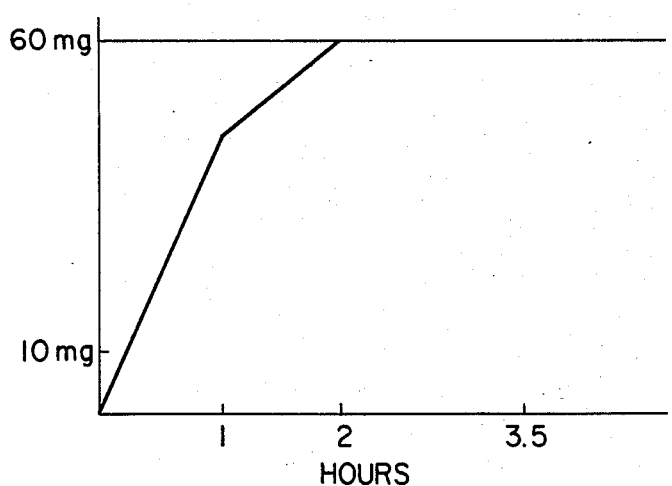
Figure 2D:
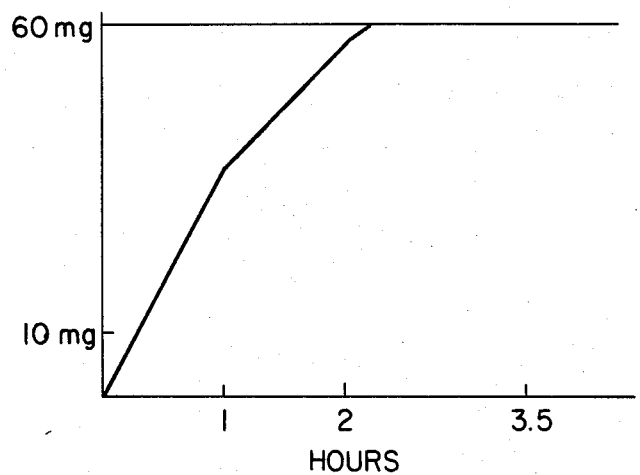
Figure 2E:
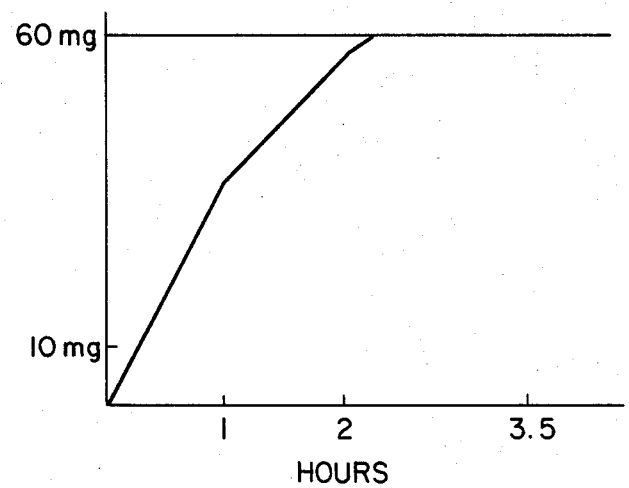

On the basis of the course of the curve in FIG. 1, tablets were then investigated which had been prepared with the use of carboxymethylcellulose with a viscosity of 3 Pa.s. The results of the liberation testing are given in FIG. 2c which show that the liberation takes place too quickly. The use of a carboxymethylcellulose with a viscosity of 0.6 Pa.s. gave a liberation characteristic lying exactly within the desired limits (FIG. 2d). The same result was obtained when using a mixture of a carboxymethylcellulose with a viscosity of 0.3 Pa.s. with a carboxymethylcellulose with a viscosity of 3.0 Pa.s (see FIG. 2e).

We claim:

1. In a process for controlling the timed release of active material from a retarded active material composition containing polysoluble adjuvant materials which is melt granulated, pressed and tableted, wherein the improvement comprises increasing the rate of release of active material by homogeneously admixing therewith prior to melt-granulating methylcellulose or carboxymethylcellulose at an increasing viscosity of from 0.02 to 40 pa.s.

2. In a process for controlling the timed release of active material from a retarded active material composition containing castor oil, stearic acid and lactose which is melt granulated, pressed and tableted, wherein the improvement comprises adjusting the rate of release of active material by homogeneously admixing therewith prior to melt granulating carboxy methylcellulose at viscosity stages of 0.05, 0.3, 0.6, 3, 6, 20 or 40 Pa.s.

* * * * *